US010288569B2

(12) United States Patent
Lee et al.

(10) Patent No.: US 10,288,569 B2
(45) Date of Patent: May 14, 2019

(54) HYDROGEL, PREPARATION METHOD THEREOF, AND PH SENSOR COMPRISING THE SAME

(71) Applicant: INDUSTRY-ACADEMIC COOPERATION FOUNDATION YONSEI UNIVERSITY, Seoul (KR)

(72) Inventors: Sang Yup Lee, Seoul (KR); Chaemyeong Lee, Gwangju (KR); Min Chul Kim, Siheung-si (KR); Jin Young Kwak, Seoul (KR); Sang Woo Park, Daejeon (KR); Young Jun Lim, Seoul (KR)

(73) Assignee: INDUSTRY-ACADEMIC CORPORATION FOUNDATION YONSEI UNIVERSITY, Seoul (KR)

( * ) Notice: Subject to any disclaimer, the term of this patent is extended or adjusted under 35 U.S.C. 154(b) by 124 days.

(21) Appl. No.: 15/427,158

(22) Filed: Feb. 8, 2017

(65) Prior Publication Data

US 2017/0146459 A1 May 25, 2017

Related U.S. Application Data

(62) Division of application No. 14/689,258, filed on Apr. 17, 2015, now abandoned.

(51) Int. Cl.
*C08K 5/29* (2006.01)
*C08K 5/42* (2006.01)
(Continued)

(52) U.S. Cl.
CPC .............. *G01N 21/80* (2013.01); *C08J 3/075* (2013.01); *C08K 5/29* (2013.01); *C08K 5/42* (2013.01);
(Continued)

(58) Field of Classification Search
CPC .. G01N 21/80; G01N 2021/7763; C08K 5/29; C08K 5/42; C08J 3/075; C08J 2305/04
See application file for complete search history.

(56) References Cited

U.S. PATENT DOCUMENTS

| 2006/0003401 A1* | 1/2006 | Lee ................... B82Y 30/00 435/34 |
| 2007/0092972 A1 | 4/2007 | Xiao et al. |

(Continued)

FOREIGN PATENT DOCUMENTS

| JP | 2002-174597 A | 6/2002 |
| KR | 10-2013-0011354 A | 1/2013 |
| KR | 10-2013-0133692 A | 12/2013 |

OTHER PUBLICATIONS

Yu-Kyoung Lee et al., "A colorimetric alginate-catechol hydrogel suitable as a spreadable pH indicator", Dyes and Pigments, vol. 108, Sep. 2014. pp. 1-6.
Changhyun Lee et al., "Bioinspired, Calcium-Free Alginate Hydrogels with Tunable Physical and Mechanical Properties and Improved Biocompatibility", Biomacromolecules, 2013 American Chemical Society, vol. 14, pp. 2004-2013.
KIPO Office Action, dated May 10, 2015, for Korean Patent Application No. 10-2014-0072332 which corresponds to the above-identified U.S. application.

*Primary Examiner* — Lore R Jarrett
(74) *Attorney, Agent, or Firm* — LRK Patent Law Firm

(57) ABSTRACT

A method for preparing a hydrogel that reversibly changes color depending on pH includes: (S10) dissolving a carboxyl group-containing polysaccharide in buffer to obtain a polysaccharide solution; (S20) adding a cross-linker solution composed of a mixture of an organic solvent and a cross-linker to the polysaccharide solution; (S30) adding, to the cross-linker-containing polysaccharide solution resulting from step (S20), an organic solution composed of a mixture of an organic solvent and a first organic compound contain- (Continued)

ing an aromatic functional group having at least one hydroxyl group bonded thereto, to form a mixture solution, and allowing the mixture solution to react; (S40) obtaining a polymer complex from the reaction mixture resulting from step (S30); and (S50) mixing the polymer complex from step (S40) with an organic dye comprising a second organic compound containing an aromatic functional group having at least one hydroxyl group bonded thereto.

6 Claims, 14 Drawing Sheets

(51) Int. Cl.
    *C08J 3/075*     (2006.01)
    *G01N 21/77*     (2006.01)
    *G01N 21/80*     (2006.01)

(52) U.S. Cl.
    CPC ... *C08J 2305/04* (2013.01); *G01N 2021/7763* (2013.01)

(56) References Cited

U.S. PATENT DOCUMENTS

| | | | | |
|---|---|---|---|---|
| 2008/0242738 | A1* | 10/2008 | Marks | C08B 37/00 514/779 |
| 2011/0077216 | A1* | 3/2011 | Kastrup | A61K 47/60 514/54 |
| 2012/0156164 | A1* | 6/2012 | Park | A61L 24/0015 424/78.3 |

* cited by examiner

HYDROGEL, PREPARATION METHOD THEREOF, AND PH SENSOR COMPRISING THE SAME

CROSS-REFERENCE TO RELATED APPLICATION(S)

This application is a division of U.S. patent application Ser. No. 14/689,258, filed Apr. 17, 2015, which claimed priority to Korean Patent Application No. 10-20140072332, filed Jun. 13, 2014, the disclosures of which are incorporated in their entireties herein by reference.

BACKGROUND OF THE INVENTION

1. Field of the Invention

The present invention relates to a hydrogel, a preparation method thereof, and a pH sensor comprising the same, and more particularly, to a hydrogel, which can substitute for conventional pH paper, is continuously usable, can be used in various applications, and reversibly changes color depending on the pH of a sample, and to a pH sensor comprising the same.

2. Description of Related Art

A technology for measuring or sensing pH is required in various technical fields. To measure or sense pH, pH paper has been widely used. The pH paper is easily available and is simple to use, but can be limitedly used for samples containing at least a certain amount of moisture or liquid-state samples, and is difficult to use for the monitoring of air pollution, the measurement of pH of moisture-free samples, the monitoring of leakage of strong acids or strong bases, etc. In addition, the pH paper is not recyclable once used, and is difficult to use in various fields. Thus, the pH paper is insufficient to function as a sensor.

SUMMARY OF THE INVENTION

Accordingly, the present invention has been made in order to the above-mentioned problems, and it is an object of the present invention to provide a hydrogel, which can substitute for conventional pH paper, can measure the pH of various samples, is continuously reusable, is in a gel form that is easily applied or coated, and can be applied in various fields, as well as a pH sensor including, the hydrogel.

To achieve the above object in one aspect, the present invention provides a hydrogel that reversibly changes color depending on the pH of a sample, the hydrogel comprising: a polymer complex wherein a first organic compound containing an aromatic functional group having at least one hydroxyl group bonded thereto is joined to a carboxyl group-containing polysaccharide by a peptide bond; and an organic dye comprising a second organic compound containing an aromatic functional group having at least one hydroxyl group bonded thereto.

The polysaccharide may be alginate, and the aromatic functional group contained in each of the polymer complex and the organic dye may be a catechol group.

In addition, the first organic compound is preferably dopamine, and the polymer complex is preferably a compound represented by the following formula 1:

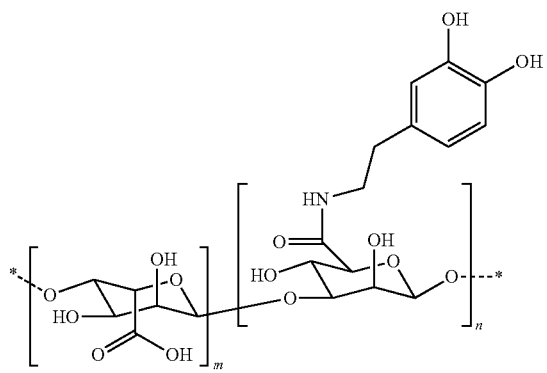

Formula 1 wherein m and n are positive real numbers; 0<m; n<1; and m+n=1.

In addition, the second organic compound may be pyrocatechol violet, and the polymer complex and the organic dye are mixed at a ratio of 10:1 to 1000:1 (weight (mg): volume (ml)). Further, the polymer complex preferably has a degree of catechol substitution of 1.3-2.0%.

The present invention also provides a pH sensor having a sample sensing region coated with the hydrogel as described above.

In another aspect, the present invention provides a method for preparing a hydrogel that reversibly changes color depending on the pH of a sample, the method comprising the steps of (S10) dissolving a carboxyl group-containing polysaccharide in buffer to obtain a polysaccharide solution; (S20) adding, to the polysaccharide solution, a cross-linker solution composed of a mixture of an organic solvent and a cross-linker; (S30) adding, to the cross-linker-containing polysaccharide solution resulting from step (S20), an organic solution composed of a mixture of an organic solvent and a first organic compound containing an aromatic functional group having at least one hydroxyl group bonded thereto, to form a mixture solution, and allowing the mixture solution to react; (S40) obtaining a polymer complex from the reaction mixture resulting from step (S30); and (S50) mixing the polymer complex with an organic dye comprising a second organic compound containing an aromatic functional group having at least one hydroxyl group bonded thereto.

In the preparation method, the polysaccharide is preferably alginate, and the aromatic functional group contained in each of the polymer complex and the organic dye is preferably a catechol group.

In addition, the first organic compound is preferably dopamine, and the polymer complex is preferably a compound represented by the following formula 1:

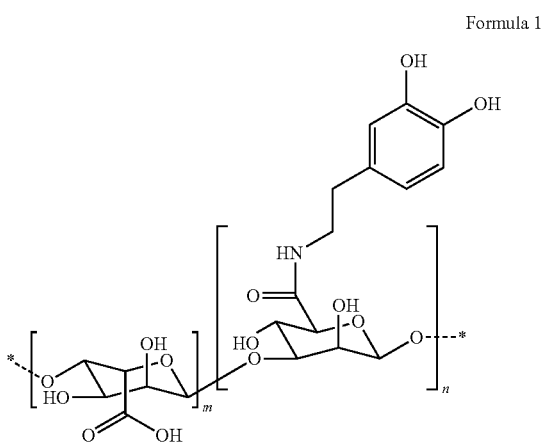

Formula 1 wherein, m and n are positive real numbers; 0<m; n<1; and m+n=1.

The organic dye may be pyrocatechol violet, and the polymer complex and the organic dye in step (S50) are preferably mixed at a ratio of 10:1 to 1000:1 (weight (mg):volume (ml)).

In addition the cross-linker is preferably a carboimide-based compound. More preferably, the cross-linker is a 1-ethyl-3-(3-dimethylaminopropyl)carbodiimide hydrochloride/N-hydroxysuccinimide (EDC/NHS) coupling agent.

The buffer may be phosphate buffered saline (PBS), and the solvent that is, used, in each of step (S20) of adding the cross-linker solution and step (S30) of adding the organic solution is methanol. In this case, step (S40) of obtaining the polymer complex preferably comprises the steps of (S41) removing the methanol by fractional distillation; and (S42) dissolving a material remaining after removal of the methanol in deionized water, followed by dialysis and freeze drying.

DETAILED DESCRIPTION OF THE INVENTION

Figure 1:
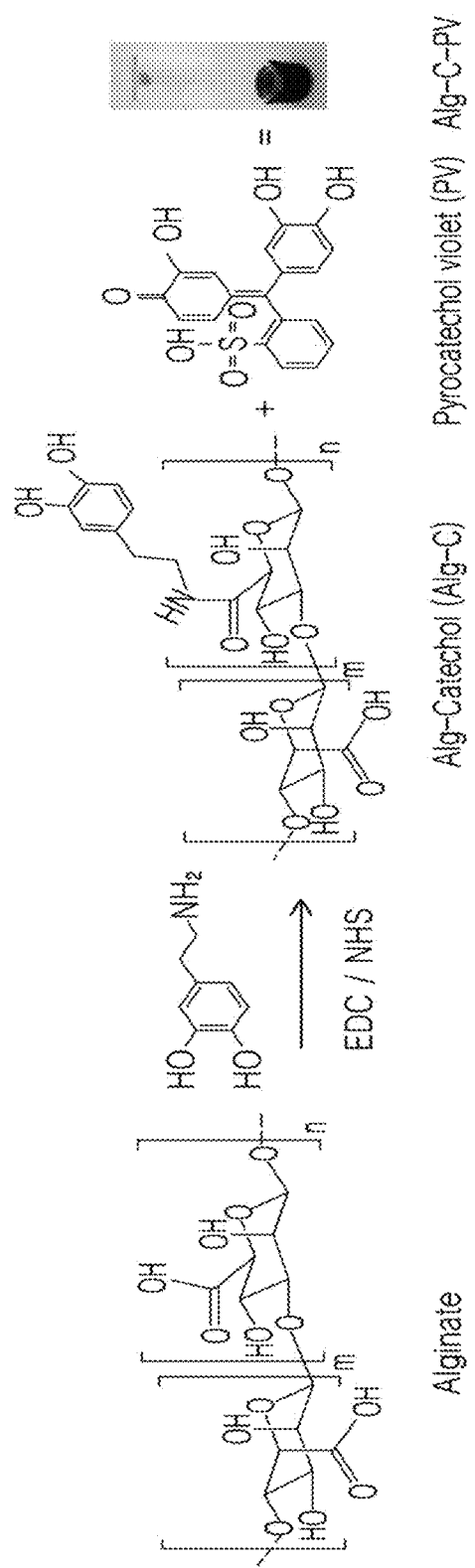
FIG. 1 is a schematic view showing a process in which a hydrogel according to the present invention is formed.

Hereinafter, preferred embodiments of the present invention will be described in detail with reference to the accompanying drawings. The terms or words used in the specification and claims should not be limited to be construed as usual or dictionary definition, but should be construed to be consistent with the technical spirit of the present invention.

In the specification, when any component is referred to as being "on" another component, it not only refers to a case where it is formed directly on the other component but also a case where a third component exists between the two components.

In the specification, when any portion "comprises" or "includes" any component, it refers to a case where it does not exclude other components, but may further comprise other components, unless otherwise specified.

The terms "first", "second", etc., are used only for the purpose of distinguishing a component from other components, and these terms are not intended to limit the scope of the present invention. For example, a first component may be named a second component, and similarly, a second component may be named a first component.

Reference numerals for steps are used for the convenience of explanation, and are not intended to indicate the order of the steps. The steps may be performed in an order different from the specified order, unless otherwise specified in the context. In other words, the steps may be performed in the same order as the specified order, or may be performed at substantially the same time, or may be performed in the reverse order.

In one aspect, the present invention provides a hydrogel that reversibly changes color depending on the pH of a sample. The hydrogel of the present invention is formed by mixing a polymer complex with an organic dye. FIG. 1 schematically shows a process in which the hydrogel of the present invention is formed.

The polymer complex is preferably a compound wherein a first organic compound containing an aromatic functional group having at least one hydroxyl group bonded thereto is joined to a carboxyl group-containing polysaccharide by a peptide bond. By using the polysaccharide and the organic compound containing an aromatic functional group having a hydroxyl group bonded thereto, a hydrogel, which have a network structure and exhibits a strong bonding strength at the molecular level, can be formed. In addition, the organic compound containing an aromatic functional group having at least one hydroxyl group bonded thereto can strongly bond to a metal or an organic or inorganic material by a metal-functional group bond, a hydrogen bond, a π-π bond or the like, and thus the hydrogel of the present invention can be easily applied in various fields.

In the polymer complex, the polysaccharide is preferably alginate. Alginate is a compound represented by the following formula 2, and is also named alginic acid In addition, alginate is a polysaccharide extracted from algae and is a polymer compound that is used as various biomaterials.

Formula 2

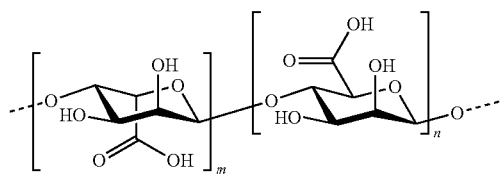

In addition, in the polymer complex, the aromatic functional group having at least one hydroxyl group bonded thereto is preferably a catechol, group that is a compound represented by the following formula 3. Living organisms have very peculiar characteristics as a result of evolution, and among them, *Mytilus coruscus* exhibits highly adhesive surface properties even in wet environments. Among adhesive components from *Mytilus coruscus*, catechol has waterproof and adhesive properties, and thus is used as a very important organic compound in various industrial fields. Low-molecular-weight and high-molecular-weight compounds containing catechol may be applied in various nanotechnology and biotechnology fields.

Formula 3

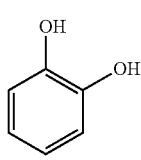

In the present invention, the first organic compound containing the catechol group is preferably a dopamine that is a compound represented by the following formula 4. Dopamine has a chemical formula of $C_8H_{11}NO_2$, and is a neurotransmitter that is produced in vivo by decarboxylation of 3,4-dihydroxyphenylamine (DOPA).

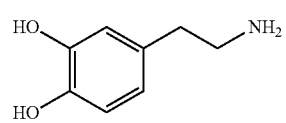

Formula 4

In a method for preparing a hydrogel according to a preferred embodiment of the present invention, a carboxyl group-containing polysaccharide, particularly alginate, is dissolved in buffer (S10), and a solution of a cross-linker in an organic solvent is added thereto (S20).

As used herein, the term "cross-linker" refers to an activating or coupling agent that activates the carboxyl group (—COOH) of a carboxyl group-containing precursor and the amine group (—NH$_2$) of an amine group-containing precursor to form a peptide bond therebetween.

The cross-linker that is used in the present invention is preferably a carboimide-based compound, and more preferably 1-ethyl-3-(3-dimethylaminopropyl)carbodiimide hydrochloride/N-hydroxysuccinimide (EDC/NHS) coupling agent.

After the cross-linker solution is added, a solution of a first organic compound, particularly dopamine, in an organic solvent, is added thereto and reacted therewith (S30). By aid of the cross-linker, a peptide bond is formed between the amine group of dopamine and the carboxyl, group of alginate, thereby forming a polymer complex that is a compound represented by the following formula 1:

Formula 1

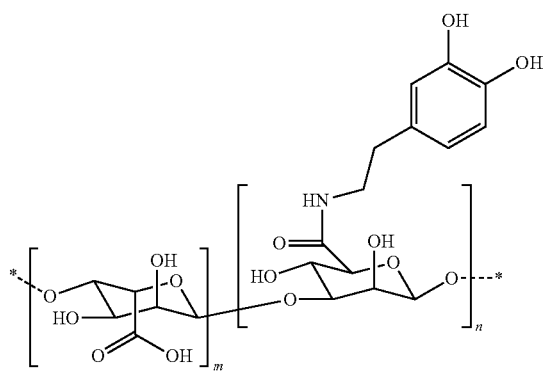

wherein m and n are positive real numbers; 0<m; n<1; and m+n=1. The polymer complex preferably has a degree of catechol substitution of 1.3-2.0%. As used herein, the term "degree of catechol substitution" refers to the ratio of the number of sites substituted with catechol to the total number of sites that can be substituted with catechol in the polymer complex.

If the degree of catechol substitution is less than 1.3%, the resulting hydrogel will exhibit poor characteristics, and it will be difficult to form a hydrogel by bonding the polymer complex with an organic dye containing a catechol group. If the degree of catechol substitution is more than 2.0%, the size or number of pores in the polymer complex will decrease so that the polymer complex cannot have a sufficient specific surface area. In addition, in this case, the swelling property of the polymer complex will decrease, and the mechanical hardness or elasticity of the polymer complex will decrease, resulting in deterioration in the characteristics of the resulting gel.

Figure 2:
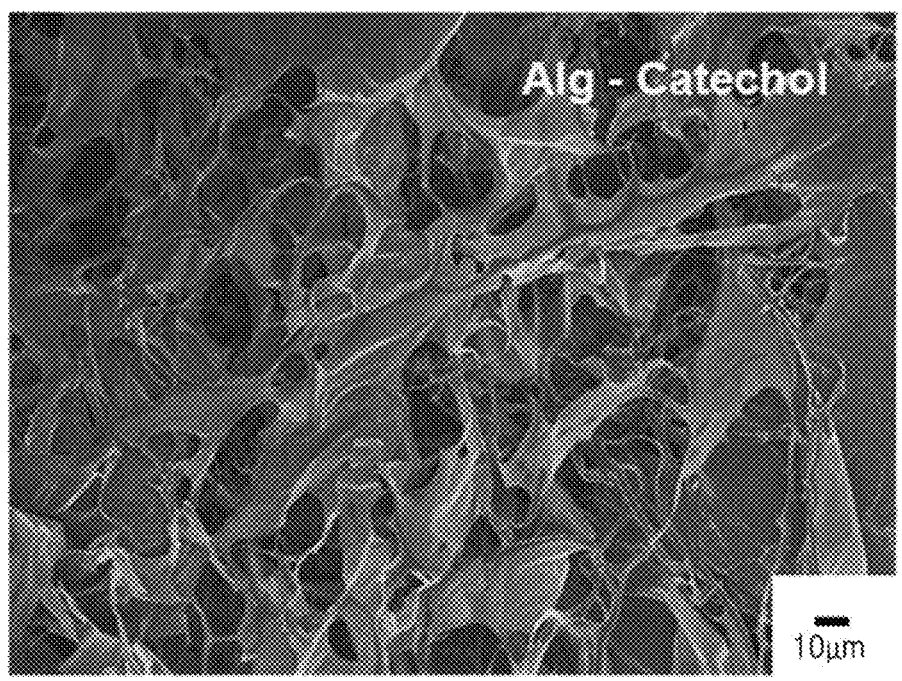
FIG. 2 is an SEM photograph of the surface structure of a synthesized polymer complex.

FIG. 2 is an SEM photograph of the surface structure of a polymer complex synthesized according to the present invention. Due to the surface structure as shown in FIG. 2, an organic dye or the like is easily penetrated into the polymer complex by a capillary effect, and water in the polymer complex is less volatile so that the polymer complex can be maintained in a discolored state for a long time.

Figure 3:
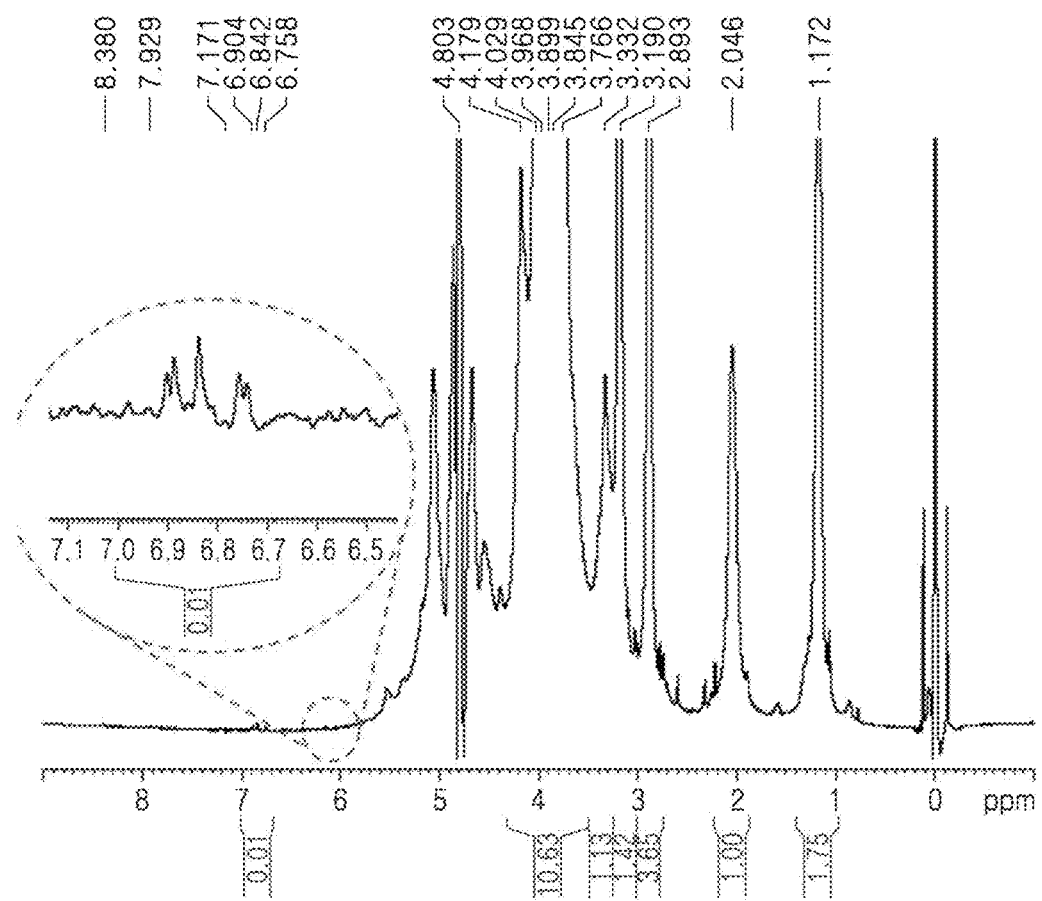
FIG. 3 is a graph showing the results of NMR analysis of a synthesized polymer complex.
Figure 4:
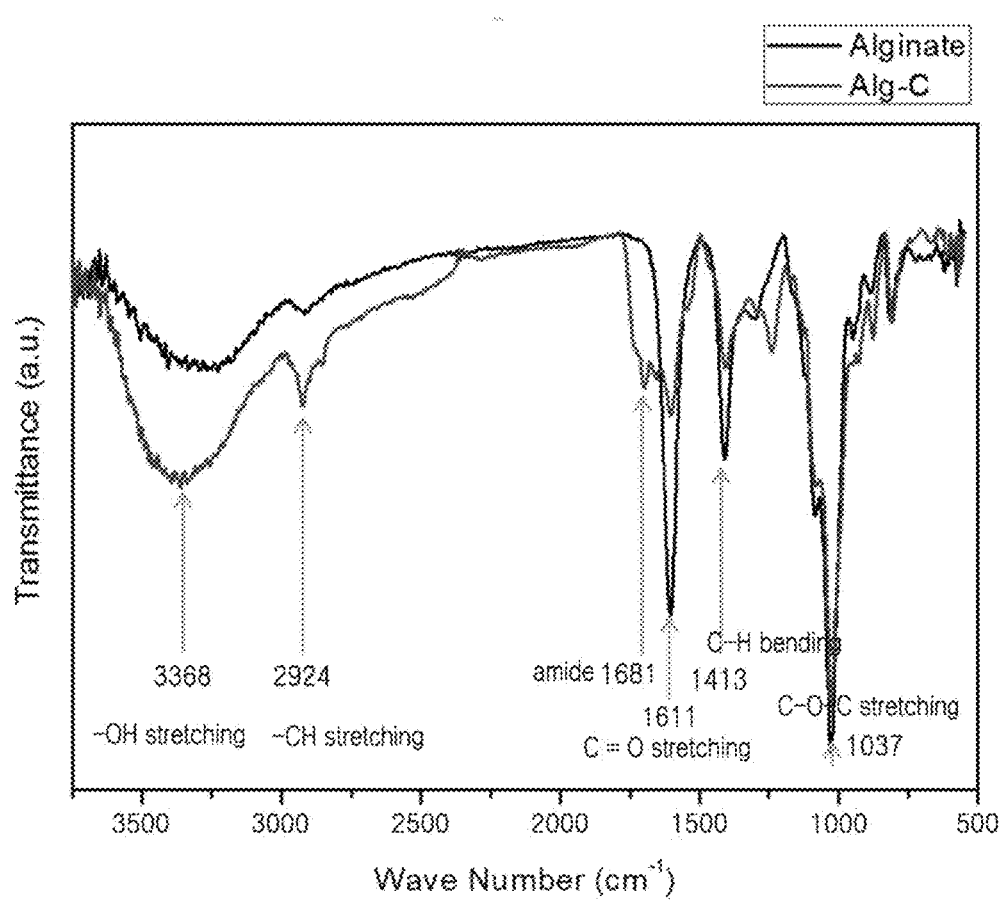
FIG. 4 is a graph showing the results of FT-IR analysis of a synthesized polymer complex and alginate.

FIG. 3 is a graph showing the results of NMR analysis of a polymer complex synthesized according to the present invention, and FIG. 4 is a graph showing the results of FT-IR analysis of the synthesized polymer complex and alginate. As can be seen in FIGS. 3 and 4, a catechol group was normally joined to alginate.

The polymer complex formed by the reaction is recovered (S40), and then the polymer complex is mixed with an organic dye containing a second organic compound, particularly pyrocatechol violet, thereby forming the hydrogel gel of the present invention (S50).

Step (S40) of obtaining the polymer complex may be performed by various methods. Preferably, the polymer complex can be recovered by removing methanol from the reaction mixture by fractional distillation at low pressure, dissolving the remaining material in deionized water at a pH of about 5 or less, dialyzing the solution for a certain time, and freeze-drying the dialyzed material.

Pyrocatechol violet is a compound represented by the following formula 5, which is a kind of sulfophthalein dye. It is dark purplish red crystalline powder with turquoise gloss. It is highly hygroscopic, is easily soluble in water, and is hardly soluble in anhydrous ethanol or an organic solvent. It is used as a metal indicator in chelometric titration of transition metal ions such as $Zn^{2+}$, $Cd^{2+}$, $Ga^{3+}$, $In^{3+}$, $Mg^{2+}$, $Pb^{2+}$ or the like. In addition, it is widely used as a reagent for high sensitivity spectroscopy in combination with a cationic surfactant.

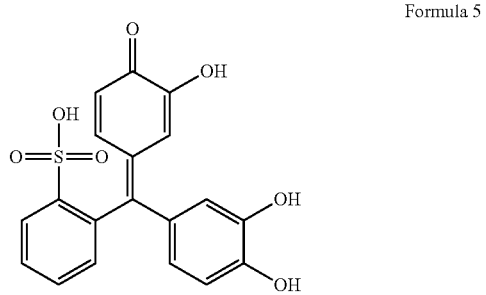 [SMILES: O=C1C=C/C(=C(/c2ccc(O)c(O)c2)c2ccccc2S(=O)(=O)O)C=C1O]

Formula 5

In the present invention, the polymer complex and the organic dye are preferably mixed at a ratio of 10:1 to 1000:1. The ratio is the ratio of the weight (mg) of the polymer complex:the volume (ml) of the organic dye, and the concentration of the organic dye is preferably 1 mM. If the mixing ratio of the polymer complex to the organic dye is lower than the lower limit of the above range, the concentration of, the polymer complex will be too low, and thus the resulting hydrogel cannot exhibit sufficient properties such as mechanical strength or viscosity, and if the mixing ratio is higher than the upper limit of the above range, the concentration of the polymer complex will be too high, and thus the resulting gel will be too hard and viscous so that it will be difficult to apply or coat.

Figure 5:
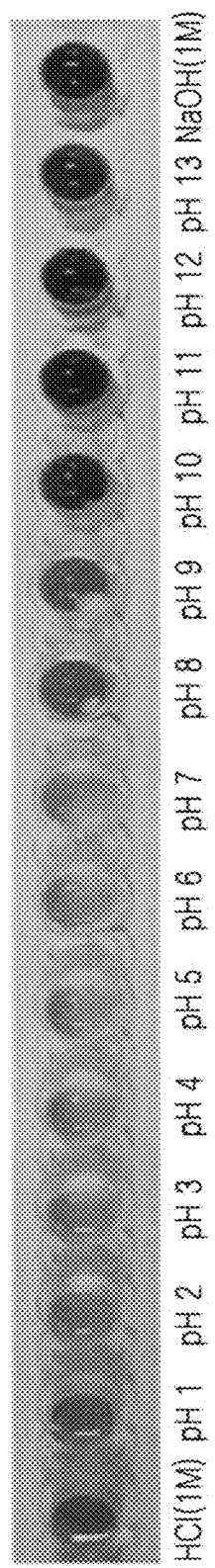
FIG. 5 is a photograph showing that the hydrogel of the present invention shows different colors depending on pH.

FIG. 5 is a photograph showing that the hydrogel of the present invention shows different colors depending on pH. As can be seen therein, the hydrogel of the present invention is basically yellow in color, and changes its color to red with increasing pH and to dark green with decreasing pH, so that the pH of a sample can be visually found.

Figure 6:
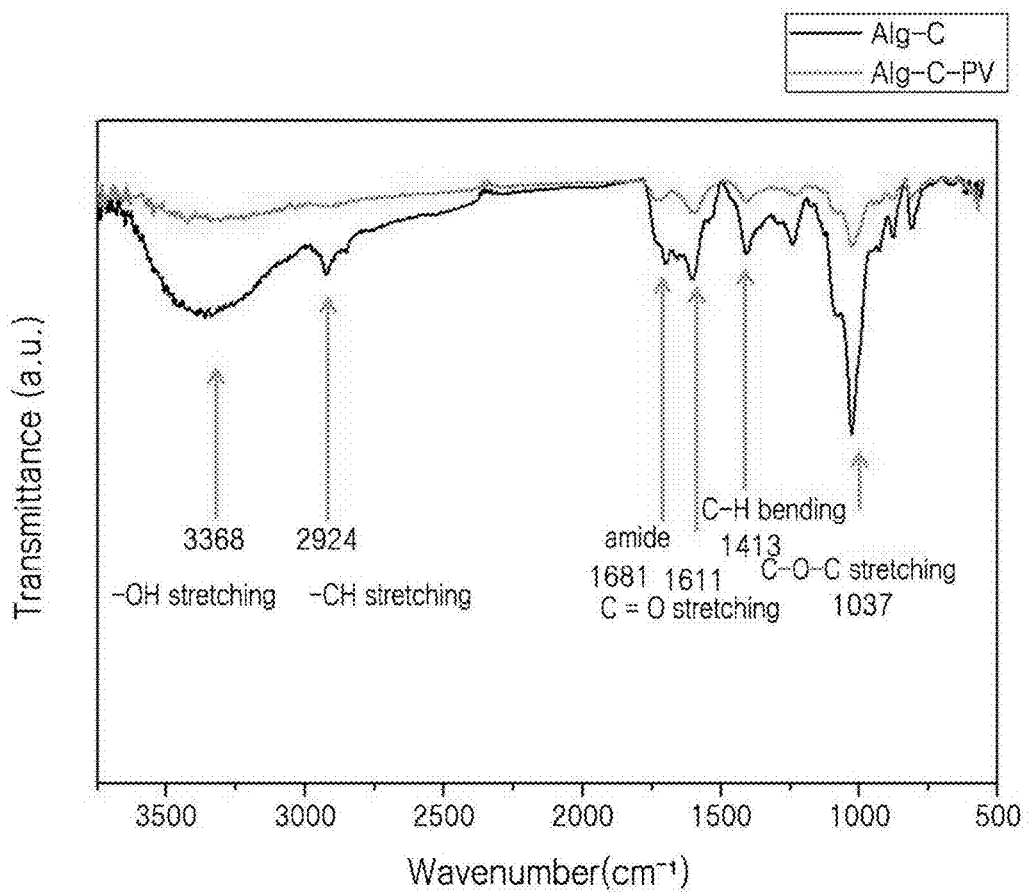
FIG. 6 shows the results of FT-IR analysis of the polymer complex (Alg-C) of the present invention and a hydrogel (Alg-C-PV) comprising an organic dye (PV) bound to the polymer complex.

FIG. 6 shows the results of FT-IR analysis of the polymer complex (Alg-C) of the present invention and a hydrogel (Alg-C-PV) comprising an organic dye (PV) bound to the polymer complex. As can be seen therein, the organic dye was normally impregnated into the polymer complex.

Figure 7:
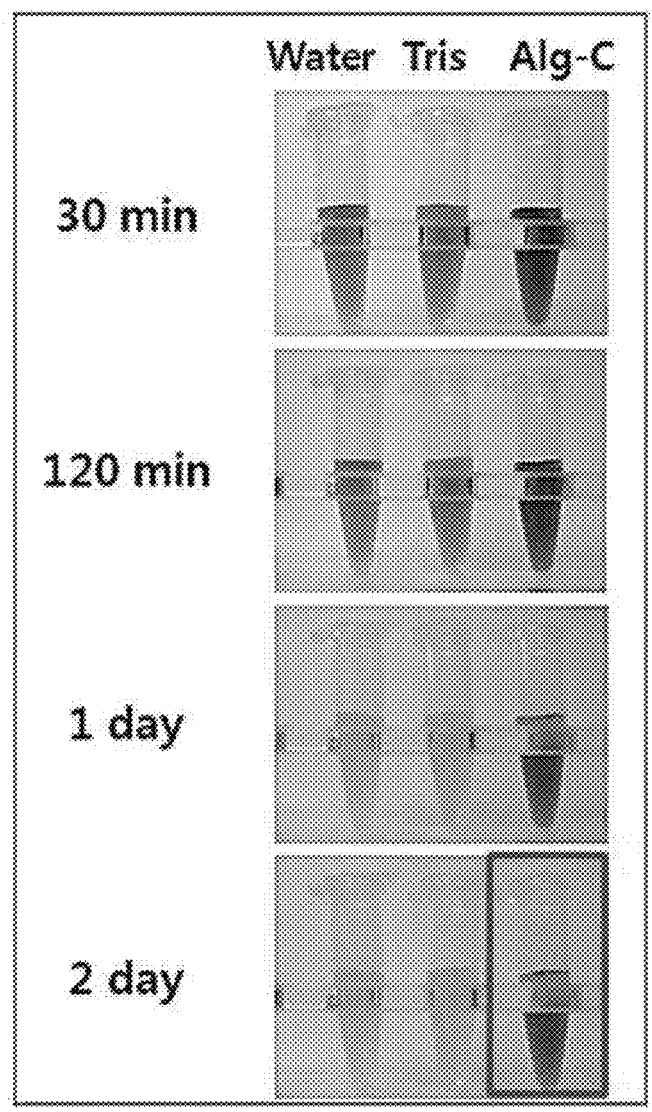
FIG. 7 is a photograph showing that a water/pyrocatechol violet mixture (left), a Tris buffer/pyrocatechol violet mixture (middle) and the hydrogel of the present invention (right) change color with time after 1M NaOH was added thereto.

The hydrogel of the present invention has an advantage in that it can maintain a pH-dependent color change for a long time, due to the strong bonding of the organic dye to the porous structure of the polymer composite at the molecular level. In connection with this, FIG. 7 is a photograph showing that a water/pyrocatechol violet mixture (left), a Tris buffer/pyrocatechol violet mixture (middle) and the hydrogel of the present invention (right) change color with time after 1M NaOH was added thereto. As can be seen in FIG. 7, the hydrogel of the present invention can be maintained in a discolored state for a longer time compared to other indicator solutions.

Figure 8:
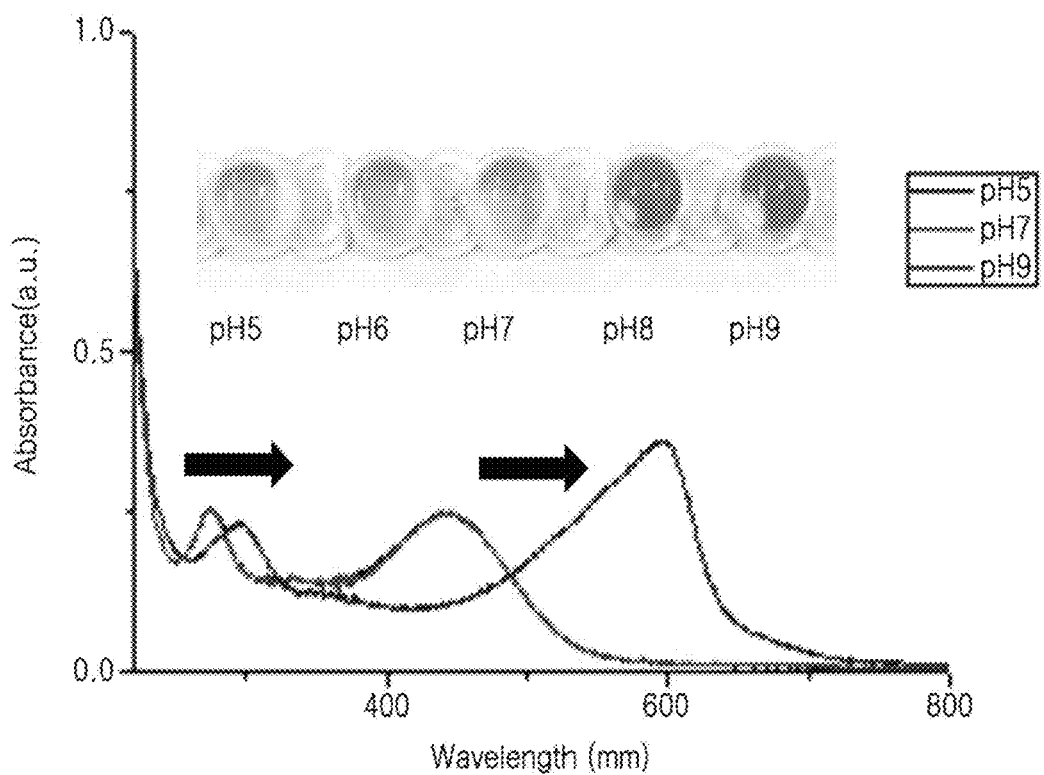
FIG. 8 depicts a photograph showing that the hydrogel of the present invention changes color with a change in pH from neutral pH to basic pH (change from pH 7 to 9), and a graph showing the UV-V is absorption peak of the hydrogel as a function of wavelength.
Figure 9:
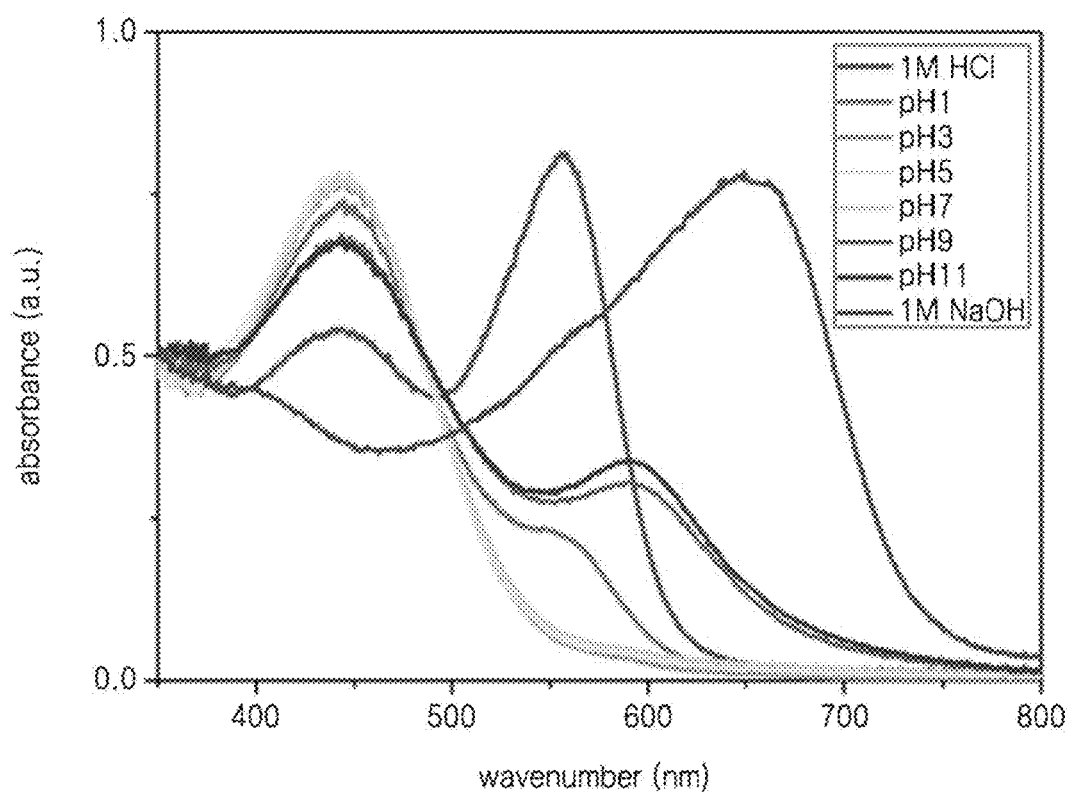
FIG. 9 is a graph showing the UV-V is absorption spectrum peaks of the hydrogel of the present invention in the pH range from strong acidic pH (1M HCl) to strong basic pH (1M NaOH).

In order to verify that the hydrogel of the present invention changes color depending on the pH of a sample, an experiment was performed. FIG. 8 depicts a photograph showing that the hydrogel of the present invention changes color with a change in pH from neutral pH to basic pH (change from pH 7 to 9), and a graph showing the UV-V is absorption peak of the hydrogel as a function of wavelength; and FIG. 9 is a graph showing the UV-V is absorption spectrum peaks of the hydrogel of the present invention in the pH range from strong acidic pH (1M HCl) to strong basic pH (1M NaOH).

Figure 10:
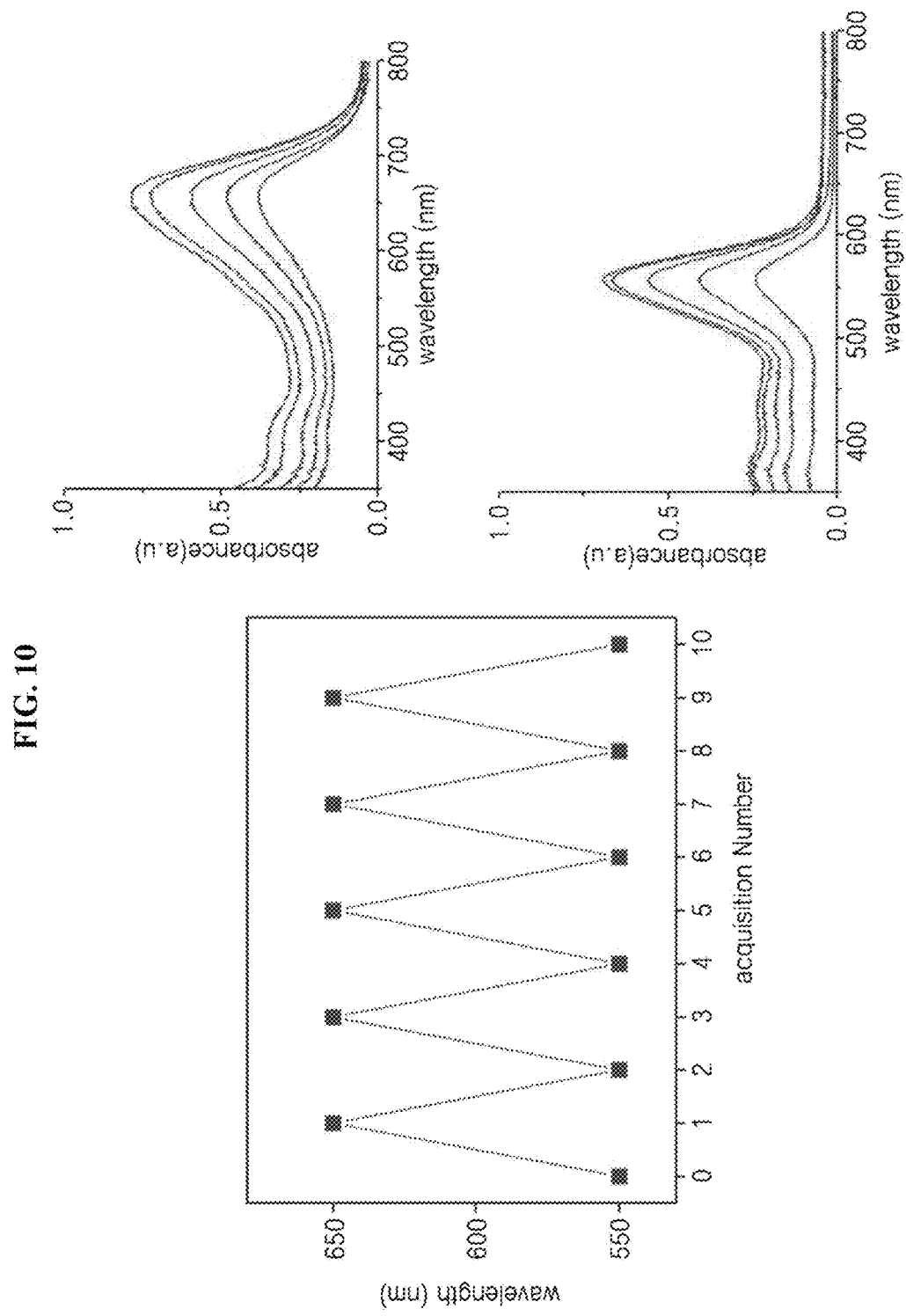
FIG. 10 is a graph showing that the maximum peak of UV-Vis spectra remained unchanged at 550 nm for a strong acid and 650 nm for a basic base when the pH value was changed five times by alternately adding the strong acid and the strong base.

In addition, the hydrogel of the present invention can "reversibly" change color in response to a change in the pH of a sample, and thus has an advantage in that it is reusable and continuously usable. FIG. 10 is a graph showing that the maximum peak of UV-V is spectra remained unchanged at 550 nm for a strong acid and 650 nm for a basic base when the pH value was changed five times by alternately adding the strong acid and the strong base. As can be seen therein, the hydrogel of the present invention can reversibly change color depending on pH, and thus is reusable.

Hereinafter, examples of the hydrogel of the present invention, a method for preparing the same, and a pH sensor comprising the same, will be described. However, these examples are merely exemplary embodiments of the present invention and do not represent all the technical ideas of the present invention. Thus, it shall be understood that various equivalents and modified examples which may replace these examples at the filing date of the present application can exist.

Example 1: Preparation of Hydrogel

The following mixtures 1 to 3 were prepared.

Mixture 1: 500 mg of alginate (molecular weight: 25,000) was dissolved in 100 ml of phosphate buffered saline (PBS; pH 7.5).

Mixture 2: 750 mg of EDC was dissolved in 30 ml of methanol.

Mixture 3: 1 g of dopamine was dissolved in 30 ml of methanol.

Mixtures 1 to 3 were mixed in the order of mixtures 1, 2 and 3 and allowed to react for 24 hours. The resulting reaction mixture was subjected to fractional distillation at 80° C. and low pressure to remove methanol. Then, the remaining material was dissolved in deionized water at a pH of 5 or less, and dialyzed against deionized water for 24 hours, followed by freeze drying, thereby obtaining 500 mg of a polymer complex.

100 mg of the obtained polymer complex (Alg-C) was mixed with 10 ml of 1 mM pyrocatechol violet (PV) solution, thereby preparing a hydrogel.

Example 2: Measurement of Mechanical Properties of Hydrogel

The mechanical properties of the hydrogel prepared in Example 1 were measured.

Figure 11:
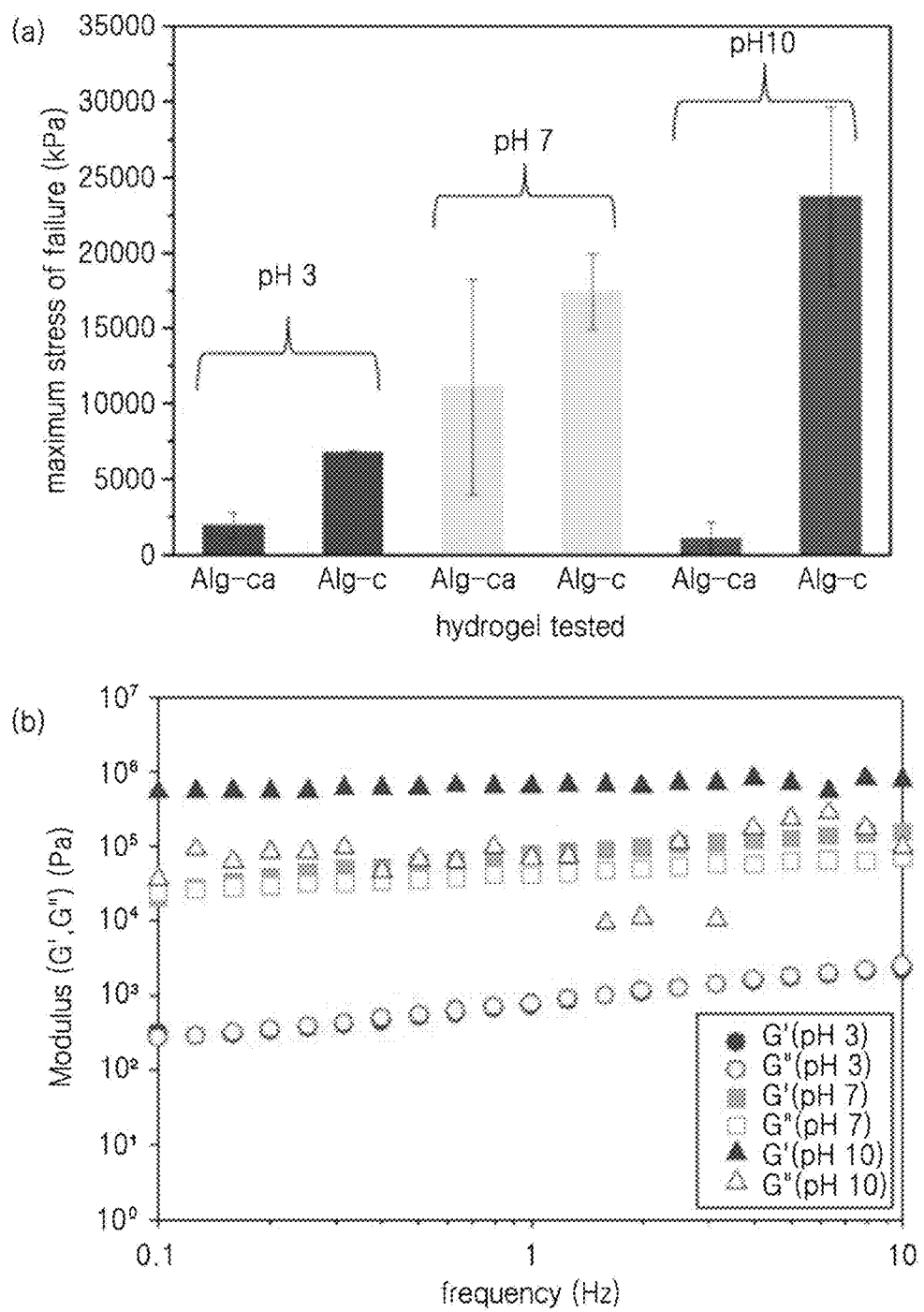
FIG. 11 is a graph showing the results of measuring the adhesion strength (FIG. 11a) and modulus (FIG. 11b) of a conventional alginate hydrogel containing calcium (Alg-Ca), and the inventive polymer complex hydrogel comprising catechol bonded to alginate (Alg-C), under varying pH conditions.

FIG. 11 is a graph showing the results of measuring the adhesion strength (FIG. 11a) and modulus (FIG. 11b) of a conventional alginate hydrogel containing calcium (Alg-Ca), and the inventive polymer complex hydrogel comprising catechol bonded to alginate (Alg-C), under varying pH conditions. Referring to FIG. 11, it can be seen that the hydrogel of the present invention exhibits excellent gel properties in terms of adhesion strength, elasticity and viscosity at pHs of 3, 7 and 10.

Example 3: Application of Hydrogel

The hydrogel prepared in Example 1 is a catechol-containing organic compound having a network structure, and thus has an advantage in that it is easily bonded to and coated on various materials.

Figure 12:
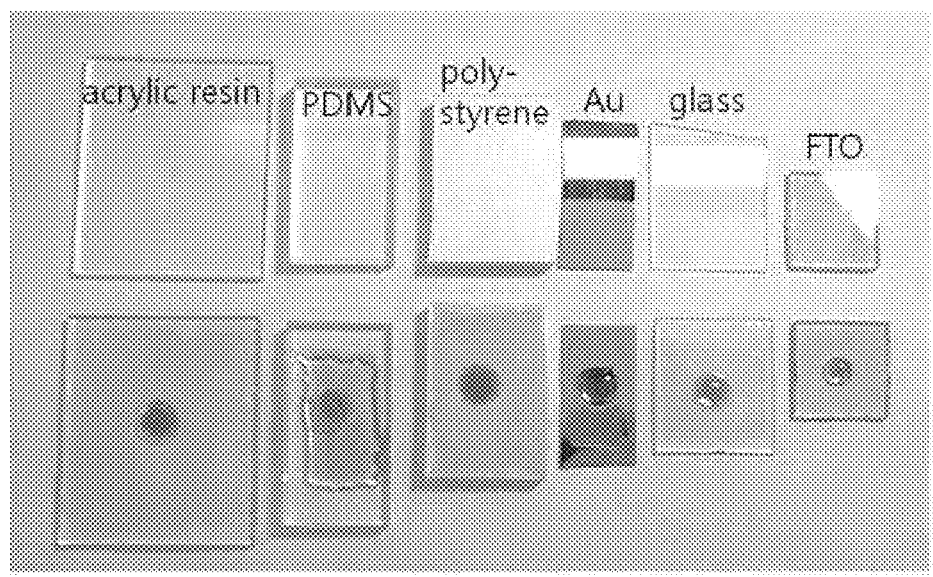
FIG. 12 is a photograph showing various substrates (from the left side, an acrylic resin substrate, a PDMS substrate, a polystyrene substrate, a gold substrate, a glass substrate, and an FTO glass substrate) obtained by applying the hydrogel of the present invention to the surfaces thereof and dropping an acidic solution or a basic solution onto the surfaces (three substrates from the left: acidic solution; and three substrates from the right: basic solution).

FIG. 12 is a photograph showing various substrates (an acrylic resin substrate, a PDMS substrate, a polystyrene substrate, a gold substrate, a glass substrate, and an FTO glass substrate, shown from the left to the right side) obtained by applying the hydrogel of the present invention to the surfaces thereof and dropping an acidic solution or a basic solution onto the surfaces (three substrates shown from the left: acidic solution; and three substrates shown from the right: basic solution).

As can be seen in FIG. 12, the hydrogel of the present invention can be easily applied to and coated on substrates made of various materials, including polymer substrates, metal substrates, and substrates made of inorganic materials, and thus can be used in various industrial fields.

For example, the hydrogel of the present invention can be applied to the fluid channel of a microfluidic device so that it enables the real-time monitoring of the pH of a sample solution flowing in the channel.

Figure 13:
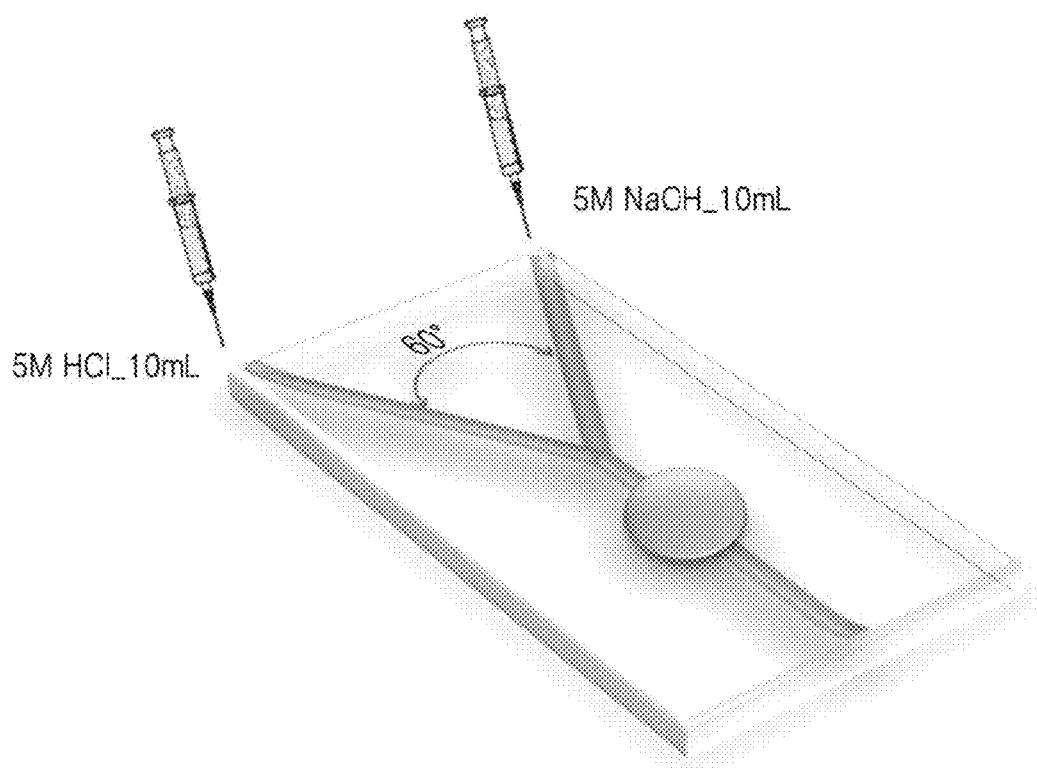
FIG. 13 is a schematic view of a microfluidic device including the hydrogel of the present invention, applied to the channel thereof.
Figure 14:
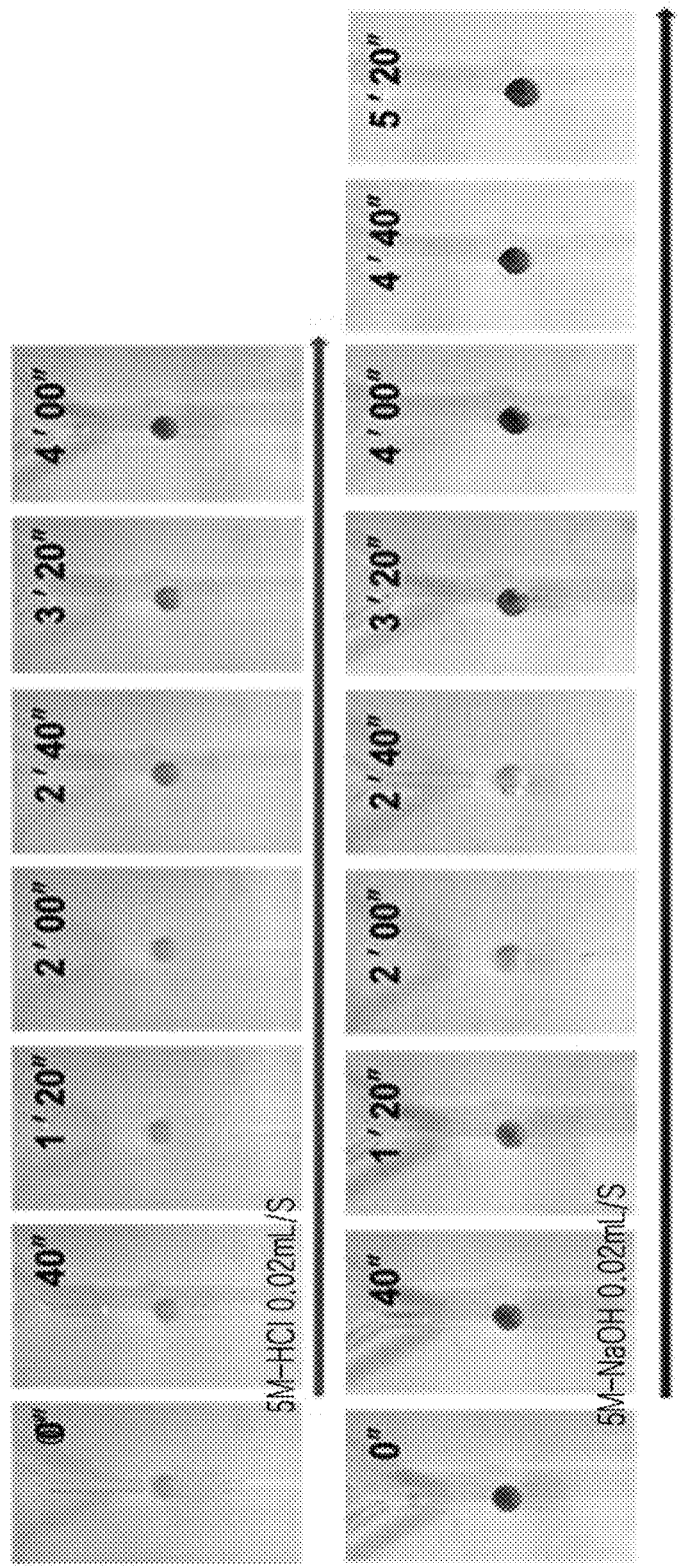
FIG. 14 is a photograph showing that the hydrogel of the present invention changes color with time when a strong acid (5M HCl, 0.02 ml/sec) or a strong base (5M NaOH, 0.02 ml/sec) is allowed to flow through a microfluidic device having the hydrogel applied to the channel thereof.

FIG. 13 is a schematic view of a microfluidic device including the hydrogel of the present invention, applied to the channel thereof, and FIG. 14 is a photograph showing that the hydrogel of the present invention changes color with time when a strong acid (5M HCl, 0.02 ml/s) or a strong base (5M NaOH, 0.02 ml/s) is allowed to flow through a microfluidic device having the hydrogel applied to the channel thereof.

As can be seen in FIGS. 13 and 14, the hydrogel of the present invention can be applied to a microfluidic device to provide a pH sensor kit that can simply and quickly measure the pH of a sample.

As described above, the hydrogel of the present invention is prepared in a gel form, and thus can be used to measure the pH of various samples. Also, it can be applied to or coated on various surfaces, and thus can be used in various industrial fields. In addition, because it reversibly changes color depending pH, it is recyclable and continuously usable.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for preparing a hydrogel, the method comprising:
    (S10) dissolving a carboxyl group-containing polysaccharide in buffer to obtain a polysaccharide solution;
    (S20) adding a cross-linker solution composed of a mixture of an organic solvent and a cross-linker to the polysaccharide solution;
    (S30) adding, to the cross-linker-containing polysaccharide solution resulting from the step (S20), an organic solution composed of a mixture of an organic solvent and a first organic compound containing an aromatic functional group having at least one hydroxyl group bonded thereto, to form a mixture solution, and allowing the mixture solution to react;
    (S40) obtaining a polymer complex from the reaction mixture resulting from the step (S30); and
    (S50) mixing the polymer complex from the step (S40) with an organic dye comprising a second organic compound containing an aromatic functional group having at least one hydroxyl group bonded thereto,
    wherein the polysaccharide is alginate, and the aromatic functional group contained in each of the polymer complex and the organic dye is a catechol group,
    wherein the first organic compound is dopamine, and the polymer complex is a compound represented by the following formula 1:

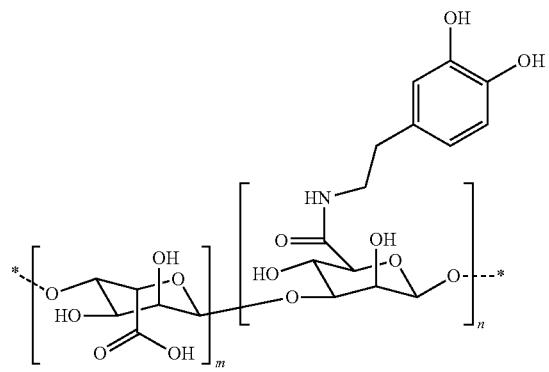

Formula 1 where m and n are positive real numbers, 0<m, n<1, and m+n=1,
    wherein the step (S50) comprises mixing the polymer complex and the organic dye are mixed at a ratio of 10:1 to 1000:1 (weight (mg):volume (ml)), and
    wherein the prepared hydrogel reversibly changes colors depending on pH.

2. The method of claim 1, wherein the cross-linker is a carboimide-based compound.

3. The method of claim 1, wherein the cross-linker is a 1-ethyl-3-(3-dimethylaminopropyl)carbodiimide hydrochloride/N-hydroxysuccinimide (EDC/NHS) coupling agent.

4. The method of claim 1, wherein the buffer is phosphate buffered saline (PBS).

5. The method of claim 1, wherein the step (S20) of adding the cross-linker solution and the step (S30) of adding the organic solution are performed with methanol as the organic solvent.

6. The method of claim 5, wherein the step (S40) of obtaining the polymer complex comprises:
- (S41) removing the methanol by fractional distillation; and
- (S42) dissolving a material remaining after removal of the methanol in deionized water, followed by dialysis and freeze drying.

* * * * *